United States Patent [19]
Curtis et al.

[11] Patent Number: 5,492,673
[45] Date of Patent: Feb. 20, 1996

[54] REAGENT SYSTEM FOR CALIBRATION OF PIPETTES AND OTHER VOLUMETRIC MEASURING DEVICES

[75] Inventors: Richard H. Curtis, Gorham, Me.; Ann E. Rundell, West Lafayette, Ind.

[73] Assignee: Artel, Inc., Westbrook, Me.

[21] Appl. No.: 89,036

[22] Filed: Jul. 9, 1993

Related U.S. Application Data

[63] Continuation-in-part of Ser. No. 843,446, Feb. 28, 1992, Pat. No. 5,298,978.

[51] Int. Cl.$^6$ ................................................ G01N 21/00
[52] U.S. Cl. ............................... 422/61; 436/8; 436/18; 73/149
[58] Field of Search ........................... 436/18, 8; 422/61; 73/3, 149

[56] References Cited

U.S. PATENT DOCUMENTS

| | | |
|---|---|---|
| 3,737,237 | 6/1973 | Zurasky . |
| 3,869,211 | 3/1975 | Watanabe et al. . |
| 3,920,580 | 11/1975 | Mast ......................................... 252/408 |
| 4,128,339 | 12/1978 | Yamazaki et al. . |
| 4,354,376 | 10/1982 | Greenfield et al. . |
| 4,805,623 | 2/1989 | Jöbsis . |
| 5,092,677 | 3/1992 | Curtis . |
| 5,125,747 | 6/1992 | Sayegh et al. . |
| 5,298,978 | 3/1994 | Curtis et al. ............................. 356/379 |

FOREIGN PATENT DOCUMENTS

0431578A2  6/1991  European Pat. Off. .

OTHER PUBLICATIONS

Cohn et al., "Precision Techniques For Measuring Liquid Quantity," Control Engineering, vol. 15, Jan. 1968, U.S., pp. 51–55.
Waring et al., "The Chemistry And Application of Dyes".
Hubs, "The Chemistry of Synthetic Dyes and Pigments," American Chemical Society, Color and Chemical Constitution of Dyes, 1970, pp. 675–676.

*Primary Examiner*—Jeffrey R. Snay
*Attorney, Agent, or Firm*—Wolf, Greenfield & Sacks

[57] ABSTRACT

A reagent system for accurately determining the volume of a pipette using a photometer is disclosed. The reagent system for use with the photometer includes a first container holding a reference solution and at least one second container holding a sample solution. A container holding the reference solution having maximum absorbance at a first wavelength is positioned in the photometer. The absorbances of the container at the first wavelength and at a second wavelength are measured. Then the optical pathlength of the container at the second wavelength is calculated from the measured absorbances at the first and second wavelengths. An aliquot of the sample solution is introduced into the container with a pipette to be calibrated. The sample solution has maximum absorbance at the second wavelength. The sample solution is mixed with the reference solution to form a mixture. Then the absorbance of the mixture in the container is measured at the second wavelength. The volume of the aliquot is calculated from the absorbance of the mixture and the optical pathlength of the container. The volume of the aliquot represents the volume of the pipette.

14 Claims, 8 Drawing Sheets

REAGENT SYSTEM FOR CALIBRATION OF PIPETTES AND OTHER VOLUMETRIC MEASURING DEVICES

This application is a continuation-in-part of U.S. patent application Ser. No. 07/843,446, filed Feb. 28, 1992, now U.S. Pat. No. 5,298,978 entitled Pipette Calibration System.

FIELD OF THE INVENTION

This invention relates to a system for accurately determining the volume of a vessel such as a laboratory pipette and, more particularly, to a reagent system for determining the volume of a pipette using a photometer.

BACKGROUND OF THE INVENTION

Pipettes are devices used to dispense liquid volumes accurately. Typically, the volumes so dispensed are less than 10 ml. Pipettes are commonly used in clinical, environmental, pharmaceutical, and chemistry laboratories. Manual action and automated pipettes perform their function typically by means of actuation of a piston within a cylinder. As the piston is drawn into the cylinder, a volume of liquid is drawn out of a reservoir. When the piston is returned to its original position that volume of liquid is expelled into a container placed so as to receive it. The volume of liquid delivered is dependent on the mechanism actuating the piston, the swept area of the piston/cylinder combination, the stroke of the piston, the condition of the various components within the system, temperature and other factors depending on the design of the particular pipette.

In may applications of pipettes it is important to know what average volume of liquid is so delivered (accuracy of delivery), and how repeatably it is delivered (precision of delivery). In the event that the accuracy and precision of delivery does not meet specified standards, then the pipette must be adjusted, repaired, or replaced. The frequency with which a given pipette must be checked depends on the criticality of results obtained in using it, and may range from daily to yearly, depending on its usage.

One way of checking the calibration of a pipette is to dispense distilled water into a container and to weigh the water so dispensed. Disadvantages of using this "gravimetric" method include the requirement for a balance of suitably high accuracy and sensitivity, a weight set with which to calibrate it, and a suitable location with a high degree of isolation from vibration and air currents; evaporation of the water sample, leading to error in the results; and the non-portability of the balance, meaning that all pipettes must be brought to the balance for checking of calibration. For large automated pieces of pipetting equipment this requirement is difficult or impossible.

An alternate method of calibrating pipettes is to use the pipette to dispense samples of dye solution or other absorbing chemical species. The sample so dispensed may be diluted with a diluent so as to reduce the absorbance to be within a range readily measured by a photometer. By knowing the concentration and absorbance properties of the dye solution, the volume of diluent, and the absorbance of the resulting mixture, the delivery volume of the pipette may be readily calculated.

This method, called a "colorimetric" method, has particular advantage for small pipette volumes (e.g. less than 100 microliters), as the weights of such small volumes of water are difficult to determine with a high degree of accuracy. Although an improvement over the "gravimetric" methods described above, known "colorimatic" assays typically suffer from a non-linearity in dye absorbance, requiring a complicated correction calculation.

OBJECT AND SUMMARY OF THE INVENTION

It is a general object of the present invention to provide an improved reagent system for calibrating the volume of a pipette or other vessel utilizing a photometer.

It is a further object of the present invention to provide a reagent system for determining the volume of a pipette with high accuracy.

It is still another object of the present invention to provide a reagent system for determining the volume of a pipette with a photometer which does not require a highly accurate container for measurement.

It is yet another object of the present invention to provide a reagent system for determining the volume of a pipette which is easy to use and low in cost.

According to the present invention, these and other objects and advantages are achieved using an improved reagent system for determining the volume of a vessel such as a pipette using a photometer. The reagent system of the present invention may be used with a specific calibration system such as the Artel PCS™ Pippette Calibration System or it may be used in connection with other, general purpose photometric equipment. An example of such an application is in checking the calibration of automated equipment which repetitively dispenses volumes of liquid into specialized cuvettes or receptacles. One such case is the equipment used to pipette samples and reagents into microtiter plates. These plates are formed of clear plastic, and typically contain 96 wells of approximately 350 µl capacity each. Once filled, the plates are transferred to automated photometric instrumentation which determines the absorbance of the contents of each of the 96 wells.

There are many other examples of equipment which accurately dispenses volumes of liquid, and whose calibration must be periodically checked. The reagent system described herein is generally suitable for use in checking the accuracy and precision of such liquid delivery mechanisms.

The reagent system of the present invention is characterized in its ability to overcome measurement inaccuracies resulting from problems of linearity, reagent preservation, and surface tension. Each of these is addressed below.

Prior reagent systems are known to be non-linear, i.e. they do not conform to Beer's Law:

$A = \epsilon c l$ where: $A$ = Absorbance
$\epsilon$ = molecular extinction coefficient
$c$ = concentration, and
$l$ = pathlength In prior reagent systems, the extinction coefficient $\epsilon$ was not constant, but instead depended on the concentration. In earlier systems, this non-linearity was partially corrected by means of a quadratic curve fit, with coefficients determined experimentally. For example, the program in the PCS™ automatically corrected the data using these coefficients. It was found in practice that the coeffcients were not stable with respect to time or temperature, leading to errors in calculated pipette volumes. In the reagent system described herein, the cause of non-linearity has been removed by chemical means, making the correction unnecessary.

It was also found that in prior systems the type and concentration of preservative was inadequate to prevent microbiological growth during storage. A new preservative (consisting of three ingredients) has been introduced which is not only more effective microbiologically, but which has no known health or environmental liabilities. It also does not react adversely with the other ingredients.

Additionally, at higher concentrations, the old sample solution would tend to "wet" the plastic pipette tips, causing small droplets to remain both inside and out, causing inaccuracy and imprecision in pipetting results. The new sample solution has a higher surface tension, and therefore wets the pipette tips much less than the old one, producing better accuracy and precision, particularly at low volumes (e.g. 10 µl and below).

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

The present invention provides methods and apparatus for accurately determining, or calibrating, the volume of a vessel such as a laboratory pipette using a photometer. The technique is typically used for calibrating the volume of pipettes in the size range from 5 microliters to 500 microliters. However, the invention can be utilized for calibrating vessels having volumes outside this range. The major components required to determine the volume of a pipette are a photometer and a calibration reagent system. A printer is preferably used to record the results.

The method comprises the steps of positioning a container in a photometer, the container holding a known amount of reference solution having maximum absorbance at a first wavelength, measuring the absorbance of the container at the first wavelength and at a second wavelength, calculating the optical pathlength of the container at the second wavelength from the measured absorbances at the first and second wavelengths, introducing an aliquot of a sample solution into the container from a vessel to be calibrated, the sample solution having maximum absorbance at the second wavelength and mixing the sample solution with the reference solution to form a mixture, measuring the absorbance of the mixture in the container at the second wavelength, and calculating the volume of the aliquot from the absorbance of the mixture and the optical pathlength of the container, based on the known volume and concentration of the reference solution and the known concentration of the sample solution, and wherein the volume of the aliquot represents the volume of the vessel.

The vessel typically comprises a pipette. The reference solution preferably comprises copper chloride dissolved in a pH 6.0 buffer and has maximum absorbance at about 730 nanometers (nm). The sample solution preferably comprises Ponceau S (Acid Red 112) dissolved in a pH 6.0 buffer and has maximum absorbance at about 520 nm.

In one preferred embodiment, the steps of introducing an aliquot of sample solution into the container, measuring the absorbance of the mixture and calculating the volume are repeated to provide multiple measurements of the vessel volume without emptying the container or moving the container from its position in the photometer.

The step of calculating the optical pathlength preferably includes correcting the optical pathlength for zero offset representative of a difference between the absorbance of the container at the first wavelength and the absorbance of the container at the second wavelength. The step of calculating the optical pathlength preferably further includes correcting the optical pathlength for a difference between the pathlength of the container at the first wavelength and the pathlength of the container at the second wavelength.

The step of calculating the volume preferably includes calculating the volume using Beer's Law.

Typically, the ambient temperature is measured before the volume of the vessel is determined. The step of calculating the optical pathlength preferably includes correcting the absorbance of the reference solution for a difference between the absorbance at the measured ambient condition and the absorbance at a reference temperature. The step of calculating the volume preferably includes correcting the measured absorbance of the mixture for a difference between the absorbance at the measured ambient temperature and the absorbance at a reference temperature. The step of calculating the volume preferably further includes correcting the calculated volume for a difference between the volume at the measured ambient temperature and the volume at the reference temperature.

In another aspect of the invention, there is provided a system for use with a photometer in determining the volume of a vessel such as a pipette. The system comprises a first container holding a predetermined volume of a reference solution containing a predetermined concentration of a first material having maximum absorbance at a first wavelength for positioning in the photometer for determination of the optical pathlength of the container, and a second container holding a sample solution containing a predetermined concentration of a second material having maximum absorbance at a second wavelength for transfer with the vessel of an aliquot of sample solution from the second container to the first container for measurement of the absorbance of the mixture of reference and sample solutions at the second wavelength and for determination of the volume of the aliquot from the optical pathlength of the first container and the absorbance of the mixture, based on the known volume and concentration of the reference solution and the known concentration of the sample solution, and wherein the volume of the aliquot represents the volume of the vessel.

In another aspect of the invention, there is provided a system for determining the volume of a vessel such as a pipette. The system comprises a photometer, a container holding a predetermined volume of a reference solution having maximum absorbance at a first wavelength positioned in the photometer, the photometer including means for measuring the absorbance of the container holding the reference solution at the first wavelength and at a second wavelength, means for calculating the optical pathlength of the container at the second wavelength from the measured absorbances at the first and second wavelengths, the photometer including means for mixing the reference solution with an aliquot of sample solution transferred to the container with a vessel to be calibrated to form a mixture and means for measuring the absorbance of the mixture at the second wavelength, and means for calculating the volume of the aliquot from the measured absorbance of the mixture and the optical pathlength of the container, based on the known volume and concentration of the reference solution and the known concentration of the sample solution, and wherein the volume of the aliquot represents the volume of the vessel.

In still another aspect of the invention, there is provided a method for measuring the optical pathlength of a container to be used for absorbance measurements at a predetermined wavelength. The method comprises the steps of positioning a container in a photometer, the container holding a reference solution having maximum absorbance at a first wavelength that is different from the predetermined wavelength, measuring the absorbance of the container at the first wavelength and at the predetermined wavelength, and calculating the optical pathlength of the container at the predetermined wavelength from the measured absorbances at the first wavelength and the predetermined wavelength.

Figure 1:
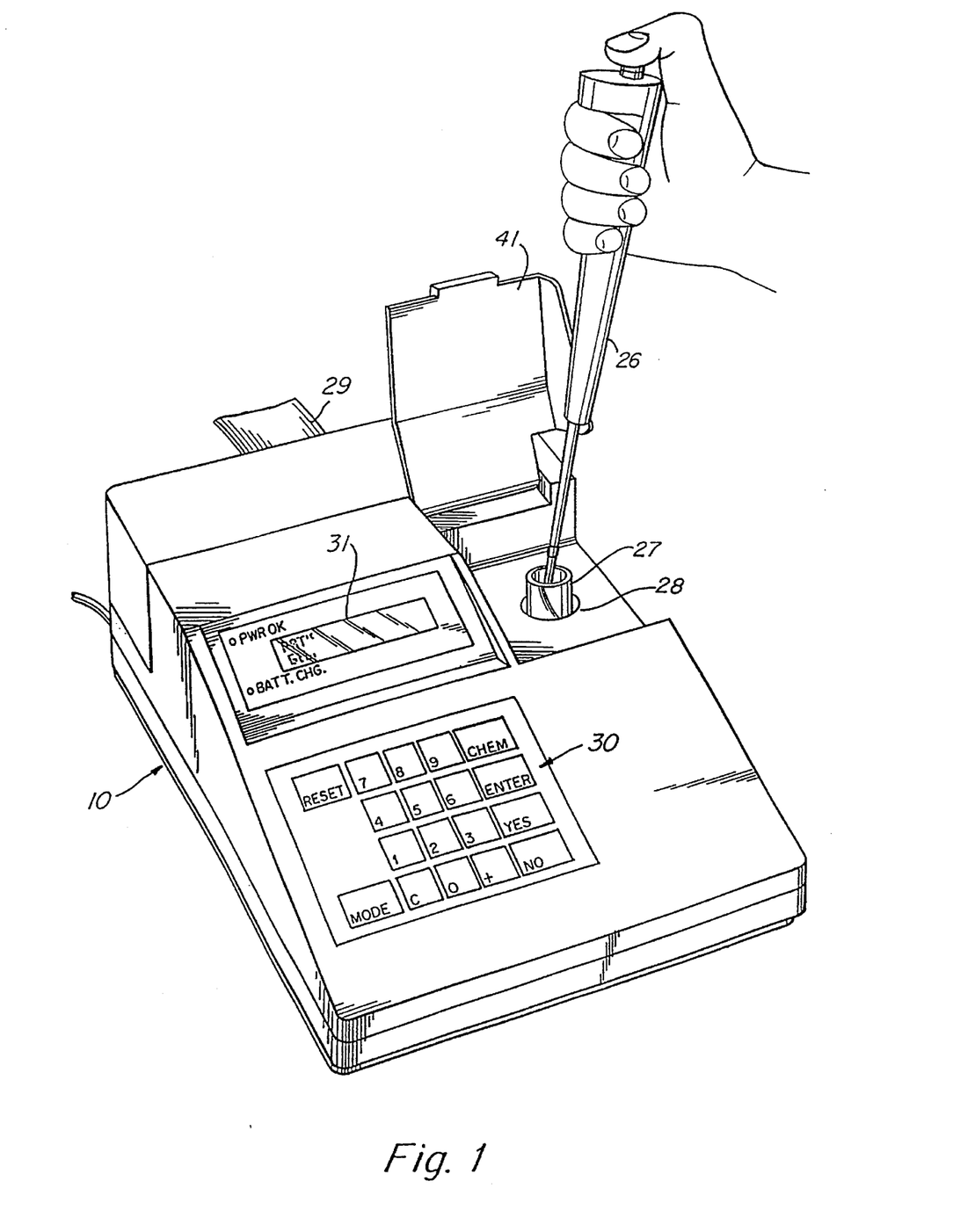
FIG. 1 is a perspective view of a photometer suitable for use in the pipette volume calibration technique of the present invention.
Figure 3:
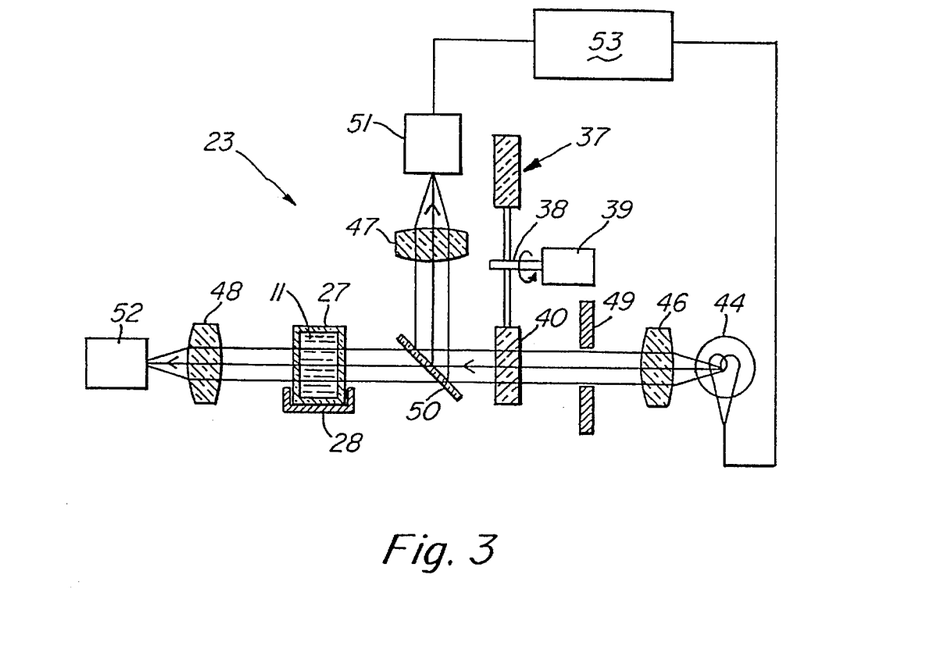
FIG. 3 is a schematic diagram illustrating the optics of the photometer utilized for absorbance measurements.
Figure 4:
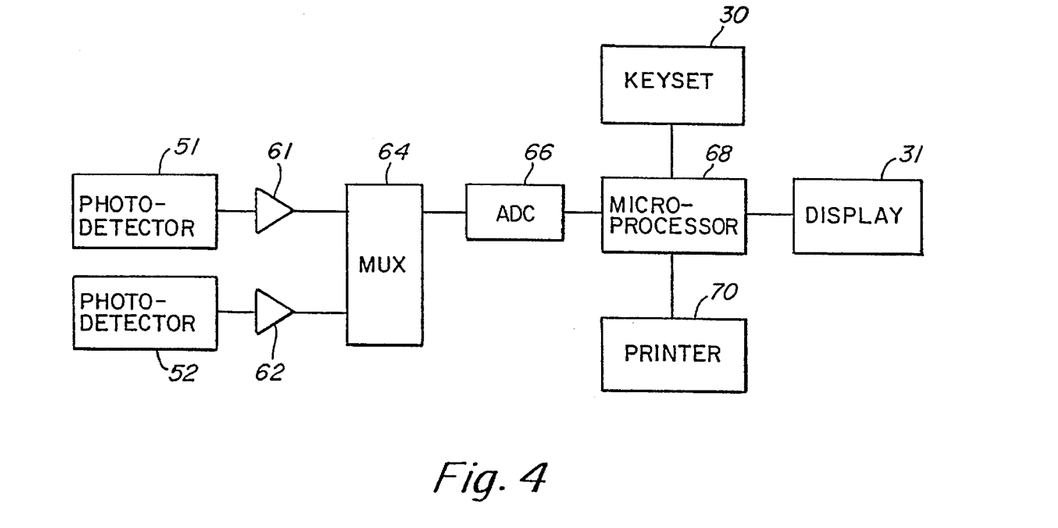
FIG. 4 is a block diagram of the major electronic components of the photometer.

A preferred photometer is shown in FIGS. 1, 3 and 4, and described more fully in U.S. Pat. No. 5,092,677, entitled "Photometer Having A Long Lamp Life, Reduced Warm-Up Period And Resonant Frequency Mixing," issued Mar. 3, 1992, and which is hereby incorporated by reference in its entirety. The photometer instrument 10 shown in FIG. 1 is a wavelength selectable photometer with the ability to handle the mixing and photometric measurement requirements of a pipette volume calibration. The instrument is operated via a keypad 30 and communicates information to the operator via an alphanumeric display 31, a printer 70 (FIG. 4) connected to a cable 29, and through audible and visual signals at specific points during and at the conclusion of each calibration. A hinged lid 41 covers a cuvette 27 (FIG. 3) containing a solution to be analyzed. The cuvette 27 is held in holder 28 in a compartment under lid 41, which allows samples to be added directly to the cuvette from a pipette 26 while in the photometer.

A schematic diagram of the optical assembly 23 of the photometer is shown in FIG. 3. Light generated by a lamp 44 is collimated to parallel rays by a lens 46, and an aperture 49 restricts the rays to a collimated beam of small diameter. The lamp is a tungsten filament bulb filled with an inert gas such as krypton or argon; this lamp has a reduced warm-up period and the inert gas minimizes evaporation of tungsten atoms from the filament, thus allowing higher operating temperatures. The beam passes through a filter 40 which selects a wavelength suitable for the test being run. The filter 40 is one of a plurality of filters mounted in a filter wheel 37 which is rotated via a shaft 38 by a filter wheel motor 39. The light beam is then split into two parts by a partially reflective beam splitter 50 which reflects about 10% of the beam to a reference photodetector 51 via a lens 47. Ninety percent of the beam passes through beam splitter 50 and through a solution 11 in cuvette 27 in cuvette holder 28. A portion of the light beam is absorbed by the solution and the remainder is transmitted through a lens 48 to a photodetector 52. The intensity of lamp 44 is regulated by feedback control circuit 53 which receives an input from reference photodetector 51 and causes the source intensity to asymptotically approach a final and stable value in a smooth and substantially exponential curve. The absorbance of the solution 11 in cuvette 27 is determined by comparing the outputs of photodetectors 51 and 52. The outputs of the reference and sample photodetectors are taken at different times while the source intensity approaches a final stable value to compensate for variations in the light source intensity over the time period during which the outputs are taken.

A block diagram of the electronics portion of the photometer is shown in FIG. 4. The outputs of photodetectors 51 and 52 are directed through preamplifiers 61 and 62, respectively, and a multiplexer 64 to an analog-to-digital converter 66. The analog-to-digital converter 66 digitizes a selected photodetector output and provides an input to a microprocessor 68. The microprocessor 68 receives the absorbance measurements from photodetectors 51 and 52 and calculates pipette volume as described in detail below. In addition, the microprocessor 68 calculates statistics and provides outputs to printer 70.

Figure 2:
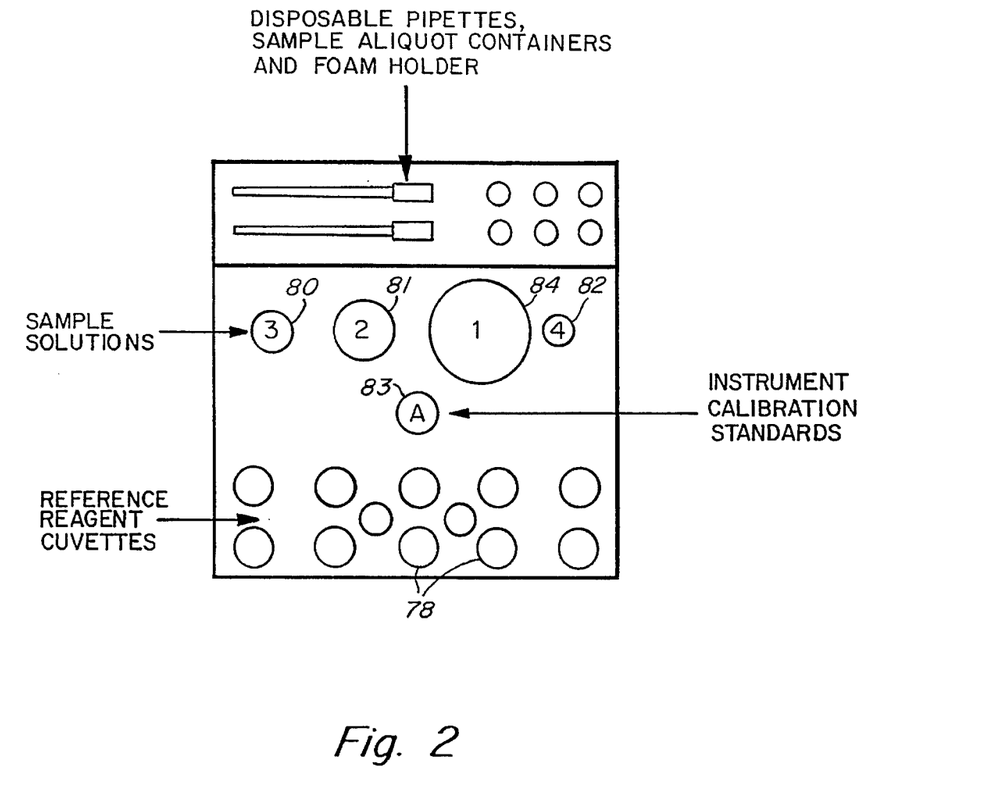
FIG. 2 is a schematic representation of a reagent system used with the photometer for pipette volume calibration in accordance with the present invention.

A suitable reagent kit for performing pipette calibration is illustrated schematically in FIG. 2. A number of reference reagent cuvettes 78, which correspond to cuvette 27 in FIG. 3, each hold a predetermined volume of a reference solution as described below. Containers 80, 81, 82 and 84 hold predetermined concentrations of sample solutions. Sample solutions with different concentrations are used for measuring pipettes in different size ranges. In a preferred embodiment, container 82 holds a sample solution for pipettes in the range of 2.0 microliters to 9.9 microliters, container 80 holds a sample solution for calibration of pipettes in the range of 10.0 microliters to 49.9 microliters, container 81 holds a sample solution for calibration of pipettes in the size range of 50.0 microliters to 199.0 microliters, and container 84 holds a sample solution for calibration of pipettes in the size range of 200.0 microliters to 5000.0 microliters. The reagent system further includes containers holding instrument calibration solution A, disposable pipettes, and sample aliquot containers.

The reagent system and the measurement technique are based on the application of Beer's Law which is expressed as follows.

$$A = Cl\epsilon \qquad (2)$$

where A is the absorbance of the solution, C is the concentration of an absorbing species, l is the pathlength of the light through the solution and $\epsilon$ is the molar absorptivity of that species. As discussed below, the absorbance measurements made by the the photometer are used to determine volume.

The calibration system uses two types of reagents, a reference (diluent) solution and a sample solution. The reference solution consists of copper chloride ($CuCl_2$) dissolved in a phthalate buffer (0.02M, pH 6.00) with a three component preservative in solution. The preservative comprises 0.1% by weight methylparaben (Methyl 4-hydroxybenzoate); 0.2% by volume Phenoxytol (2-phenoxyethanol), and 0.1% by weight EDTA, TSS (Ethylenediametetraacetic Acid, Tetrasodium Salt). The reference solution further comprises an anti-agglomeration agent such as PEG 200 (polyethylene glycol, MW=200). For use in equipment other than the Artel PCS™ system described above, the PEG 200 is used at 3% by volume. For the PCS™ system, PEG 200 is used at 10% by volume. In this latter case the reference solution further comprises $6.588\times10^{-3}$M copper chloride dihydrate ($CuCl_2 \cdot 2H_2O$) and an additional $6.588\times10^{-3}$M EDTA,TSS. The additional EDTA,TSS acts as a chelating agent for copper ions, serving the dual purpose of enhancing absorbance of the copper ions while preventing their interaction with the Ponceau S dye.

The reference reagent cuvettes 78 shown in FIG. 2 are prefilled with exactly 4.75 milliliters of reference solution and are tightly capped.

The sample solution is made using the same buffer and preservative composition as the reference solution to which is further added the dye Ponceau S (Acid Red 112){3 hydroxy-4-[2-sulfo-4-(4-sulfophenylazo)phenylazo]-2,7-naphthalenedisulfonic acid, tetrasodium salt}. The dye is present at a concentration of about $2.5\times10^{-5}$M–$2.0\times10^{-2}$M depending upon the intended application. As indicated above, there are three concentrations of sample solutions to permit a range of pipette volumes to be calibrated.

Figure 5:
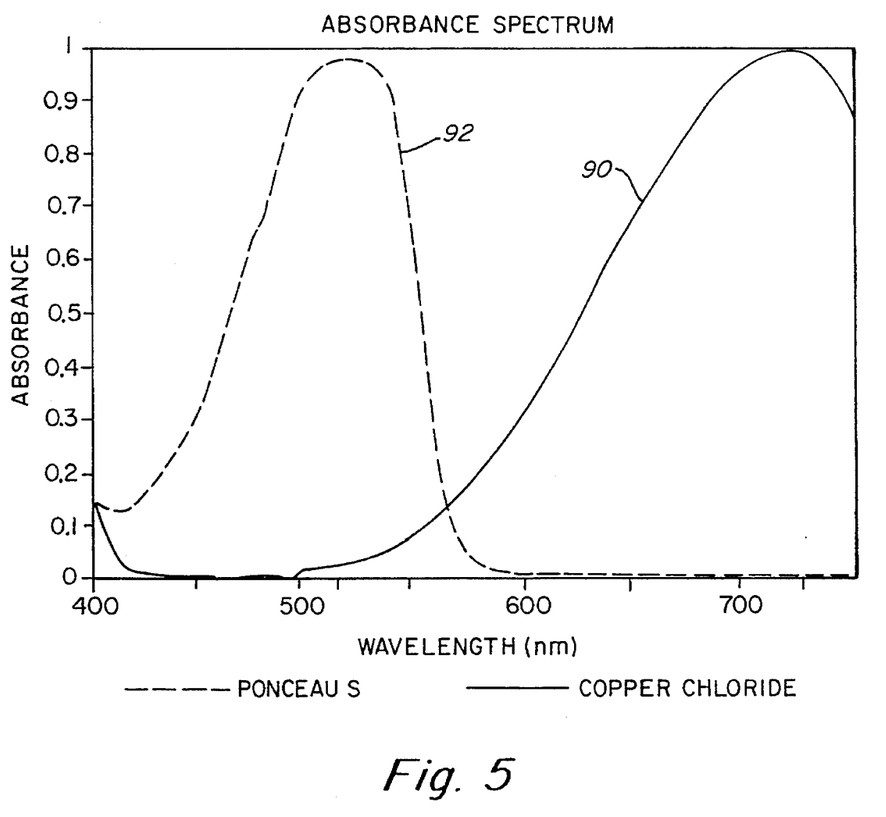
FIG. 5 is a graph of absorbance as a function of wavelength showing the absorbance spectra for copper chloride and Ponceau S.

The reference and sample solutions constitute dyes which work together to permit accurate pipette volume calibration. As shown in FIG. 5, the dyes have different absorbance peaks. As indicated by curve 90 in FIG. 5, copper chloride (dye B) has an absorbance peak at about 730 nm. As indicated by curve 92, Ponceau S (dye A) has an absorbance peak at about 520 nm. Furthermore, there is little overlap between the absorbance spectra. At 520 nm, the absorbance of copper chloride is relatively small and at 730 nm, the absorbance of Ponceau S is relatively small.

The cause of the non-linearity in known reagent systems is believed to be the agglomeration of dye molecules in the presence of other ions. The dye alone, in aqueous solution, is linear over a wide range. The presence of other ingredients introduces ions which cause non-linearity.

Other ingredients which are desirable in the subject reagent systems include a buffer to stabilize the pH, since the absorbance properties of the dyes investigated all depended on the pH of the solution; and preservatives to prevent microbiological growth.

In the case of reagents used in the Artel PCS™ Pipette Calibration System, a second absorbing species with a peak well away from that of the first dye, and with little or no absorbance in the region of the first dye's peak is used as well.

Each of these other ingredients tends to cause agglomeration, as can be determined by absorbance measurements for a sequence of dilutions. Ponceau S, and all other organic dyes tested exhibited the same general behavior.

Figure 8:
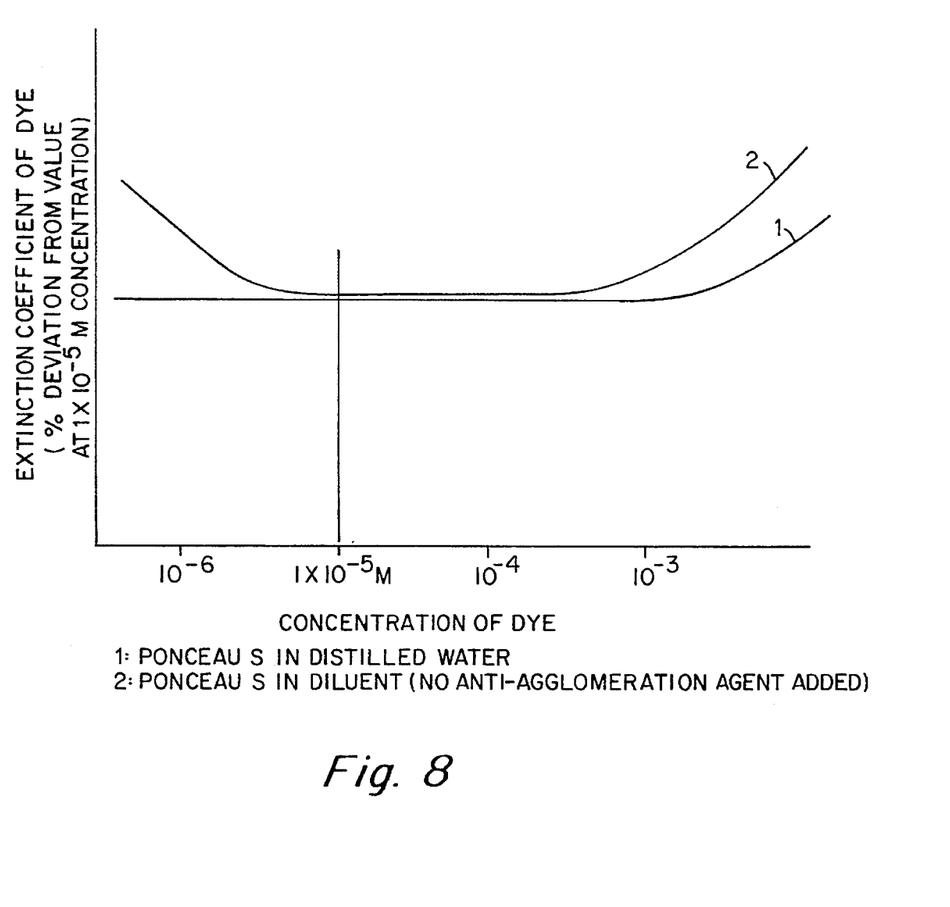
FIG. 8 is a graph of the extinction coefficient of Ponceau S in distilled water and a buffer solution.

The agglomeration of dye molecules causes non-linearity to take the form shown in FIG. 8. The data are taken from experimental results using the ingredients described above. Curve 1 represents Ponceau S in distilled water, and curve 2 represents Ponceau S in the diluent described above without the addition of an anti-agglomeration agent. Results of this general nature have been observed for a number of different formulations in which organic dyes are in solution with salts in appreciable concentration (greater than that of the dye).

In order to prevent agglomeration, two means are employed.

1. Concentrations of all ingredients other than the dye are kept to an absolute minimum. For instance, the buffer is adequately effective at 0.02M, compared to known buffers at 0.10M.

2. An anti-agglomeration agent is added to minimize agglomeration of dye molecules. Agents which have been tried and which function to some degree are:

ethylene glycols
diethylene glycols
triethylene glycols
polyethylene oxides
polyethylene glycols (MW in the range 200 to 10,000)
pyridines, and
propylene glycols.

Figure 9:
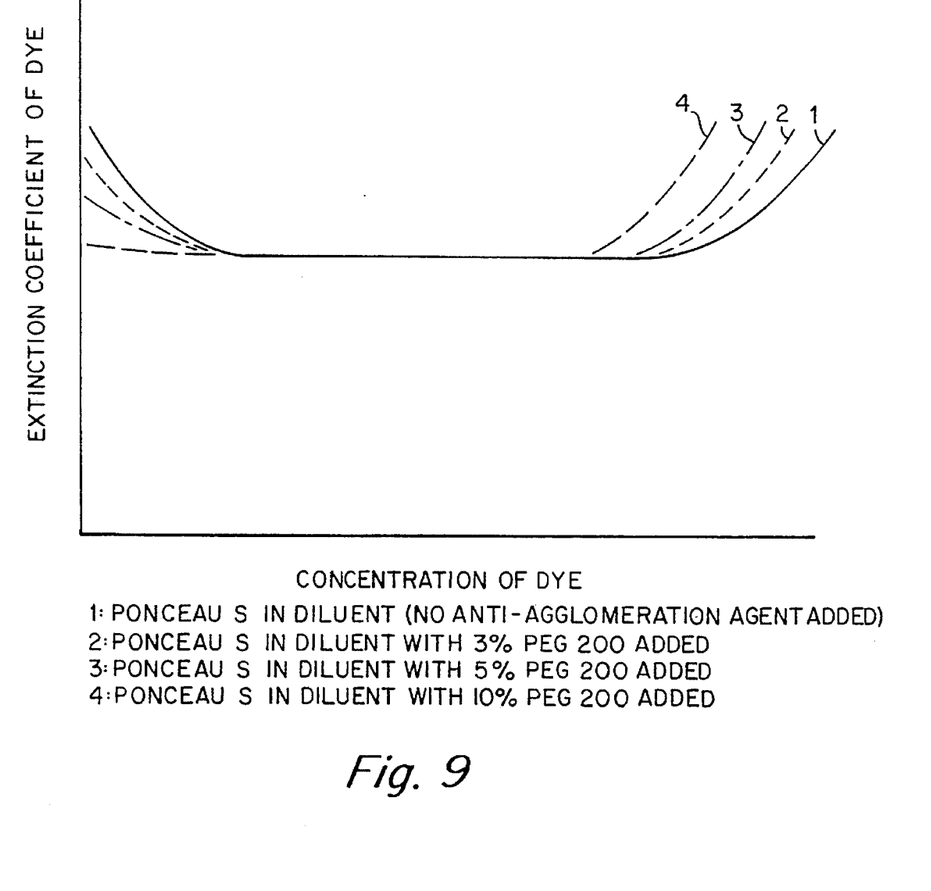
FIG. 9 is a graph of the extinction coefficient of Ponceau S in a buffer solution with varying amounts of an anti-agglomeration agent added.

The most effective agent is believed to be polyethylene glycol, molecular weight 200 (PEG 200). The amount required to assure adequate linearity depends of the concentration of other ingredients. In the present formulation, 10% PEG 200 is added to the reference or dilutent solutions. FIG. 9 shows the effect of adding PEG 200 in varying concentrations to the formula described above. In particular, curve 1 represents Ponceau S in the diluent described above without the addition of an anti-agglomeration agent. Curves 2–4 represent the solution of curve 1 with the addition of the anti-agglomeration agent PEG 200 in the amounts of 3%, 5%, and 10%, respectively. It can be seen that the non-linearity at the low concentration end of the scale is removed, although non-linearity at the high end is made worse, with an onset at lower concentration. For purposes of using an organic dye as an absorbance standard, it is essential that the low end be made linear. Accordingly, the high end non-linearity can be avoided by never using concentrations above the point at which non-linearity begins.

Previous reagent systems used sodium azide, at 0.01% w/w concentration as a preservative. At that concentration, microbiological growth occurred, degrading the optical clarity of the reagents. Due to suspected health effects of sodium azide, its use has been discontinued, and a substitute consisting of: 0.1% w/w Methylparaben, 0.2% v/v Phenoxytol, and 0.1% w/w EDTA, Tetrasodium salt is employed.

The first two compounds are well known in the cosmetics industry where they provide effective and safe control of microbiological growth. The EDTA is added to potentiate the effect of methylparaben on gram negative bacteria.

This preservative combination has been extensively tested in conjunction with the buffer (phthalate buffer, 0.02M, pH 6.00) and dye (Ponceau S). It has no measured adverse effect on the dye after 3 months of testing.

The previously used dye Acid Red 1 caused low surface tension in concentrated aqueous solution, leading to inaccuracy and imprecision in pipetting results. A possible cause of this low surface tension is the presence of impurities in the commercially available preparations. The current dye, Ponceau S (Acid Red 112), is available in highly purified form, which may be the reason for the high surface tension of even very concentrated solutions (up to 20 times that of the previous Acid Red 1 solutions). These solutions pipette in very similar manner to distilled water, which is the usual standard of comparison.

The technique for determining pipette volume in accordance with the present invention is based in general on first determining the optical pathlength of the cuvette that is placed in the photometer for holding the solutions to be measured. It will be understood that variations in thickness and absorbance of the cuvette walls as well as variations in the inner diameter of the cuvette affect the optical pathlength. In practice, it has been found that cuvettes of acceptable cost vary by about 2% in optical pathlength. Furthermore, the cuvettes may not be perfectly round and thus vary in optical pathlength depending on their orientation in the photometer. Since it is desired to determine pipette volume with an inaccuracy of 1% or less, it is necessary to determine the optical pathlength of each cuvette when positioned in a predetermined orientation in the photometer.

After the optical pathlength of the cuvette has been determined, the volume of the pipette being calibrated is determined. In general, the volume measurement technique is based on dilution of the reference solution in the cuvette with a sample solution transferred into the cuvette by the pipette being calibrated. The aliquot of sample solution transferred into the cuvette corresponds to the volume of the pipette. The reference solution and the sample solution are mixed, and the absorbance of the mixture is measured at the wavelength where the sample solution has maximum absorbance. The increase in absorbance of the mixture depends on the volume of the sample solution added from the pipette being calibrated. The technique for pipette volume calibration is described in detail below.

Figure 6:
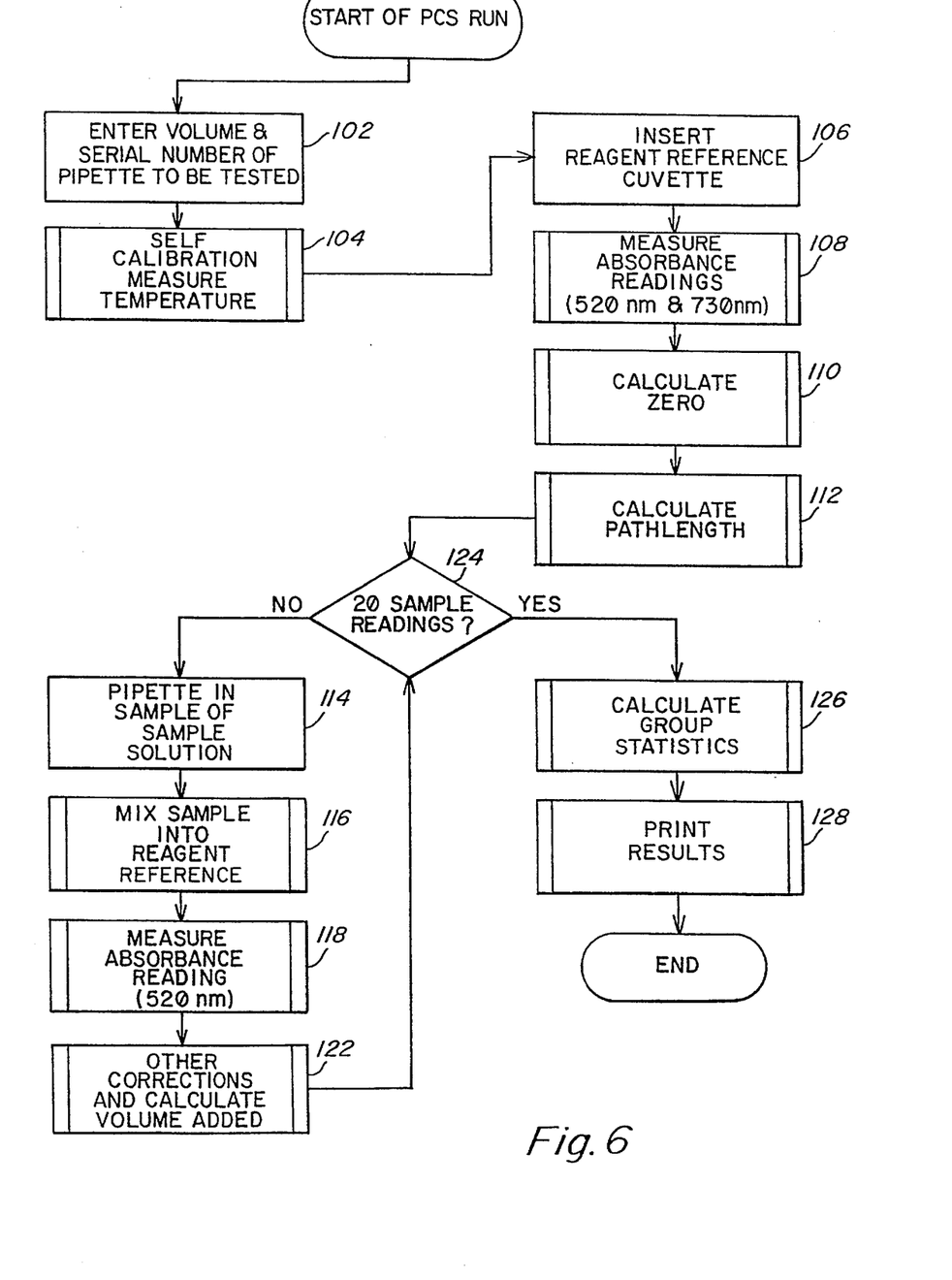
FIG. 6 is a flow diagram of the method for pipette volume calibration in accordance with the present invention.

A flow diagram of the volume calibration procedure in accordance with the present invention is shown in FIG. 6. Initially, the nominal volume and serial number of the pipette to be calibrated is entered through keypad 30 in step 102. This information is used subsequently in printing the results of the calibration. Then the photometer performs a self-calibration in step 104, during which the ambient temperature is measured and stored for later use. The photometer includes a thermistor for measurement of ambient temperature. Then, the user inserts a reference reagent cuvette 78 into the photometer through hinged lid 41 in step 106. The reference reagent cuvette 78 is located in the photometer in the position of cuvette 27 shown in FIG. 3 so that the light beam passes through the cuvette and the solution contained in it. As indicated above, the reference reagent cuvette 78 contains a predetermined volume of copper chloride dissolved in a pH 6.0 buffer. The copper chloride has a known concentration, typically 0.006588 molar. The photometer makes absorbance measurements of the reference reagent cuvette at 520 nm and 730 nm in step 108. Then, the zero is calculated in step 110 and the pathlength of the reference reagent cuvette 78 is calculated in step 112.

In a preferred embodiment, the reference reagent cuvettes 78 are borosilicate glass vials having a nominal diameter of 21 millimeters. The nominal pathlength is 18.4 millimeters. The terms "cuvette" and "vial" are used interchangeably herein to refer to the container that is placed in the photometer for absorbance measurements. As indicated above, there is a 2% tolerance on the pathlength and the vials are not perfectly round, so that the measured pathlength depends on the orientation of the vial in the photometer.

The relatively poor accuracy of the pathlength specification would degrade the overall accuracy of the volume calibration if it were not corrected. The technique selected to deal with this inaccuracy is to measure the pathlength of each vial as it is positioned in the photometer ready for use. Thus, variations in pathlength, due either to orientation of the vial in the photometer or due to diameter variations, are taken into account as the results are calculated.

The optical pathlength for each vial is determined individually in the following way. As indicated above, a copper chloride dye solution having an absorbance peak at 730 nm is used as a reference solution in the reference reagent cuvette 78. The absorption of copper chloride at a wavelength of 520 nm is quite small. After the cuvette is loaded into the photometer, absorbance measurements are made at these two wavelengths (step 108). The difference in absorbance measurements at the two wavelengths is related to the difference in absorptivities according to Beer's Law as given in Equation (1) above. These values are used to solve for the pathlength l as follows.

$$l = \frac{A_{730} - A_{520}}{C_B (\epsilon_{B2} - \epsilon_{B1})} \quad (2)$$

where l is the optical pathlength, $A_{520}$ is the measured absorbance at 520 nm, $A_{730}$ is the measured absorbance at 730 nm, $C_B$ is the known concentration of dye B (copper chloride) and $\epsilon_{B2}$ and $\epsilon_{B1}$ are the absorptivities at wavelengths of 730 nm and 520 nm, respectively.

Two minor corrections are made to the calculated optical pathlength in order to make the determination more accurate. A first correction is made for zero offset. The vial itself absorbs slightly differently at the two wavelengths so that a vial filled with distilled water shows a difference in absorbance between 520 nm and 730 nm. Typically, the difference in absorbance is approximately 0.01. There is a also a slight instrument variation in this measurement.

The zero offset is measured each time the photometer is turned on. The display 31 prompts user to insert the CAL A calibration vial 83 (FIG. 2), which contains distilled water without dyes. The difference in absorbance (zero offset), $A_{off}$ is measured and stored for use later in the day. The zero offset is used to correct the absorbances measured for the reference reagent cuvette at run time, providing a corrected pathlength of $$l' = \frac{A_{730} - A_{520} - A_{OFF}}{C_B (\epsilon_{730} - \epsilon_{520})} \quad (3)$$

It is assumed that the reference reagent cuvette 78 has the same zero offset (within 0.001) as the CAL A calibration vial 83.

A second correction accounts for the fact that the effective optical pathlength of the vial is not independent of measurement wavelength. The reason for this dependence is that the vial is round, and the light beam entering the vial is fairly broad (about 4 millimeters in diameter) and is refracted at the glass-air interface, both on entering and leaving the vial. The amount of refraction is dependent on the index of refraction of the glass at the measurement wavelength. The dependence of optical pathlength on wavelength is measured as described below to provide a correction factor $F_{\lambda corr}$ to be used in the pathlength calculation. After the correction factor $F_{\lambda corr}$ is determined, it is applied to all calibration calculations. It is not necessary to remeasure the correction factor for each vial, since the value is consistent between vials and depends only on the dispersion of the glass type used in making the vial. The optical pathlength at 520 nm is thus given by $$l_{520} = \frac{F_{\lambda corr} (A_{730} - A_{520} - A_{OFF})}{C (\epsilon_{B2} - \epsilon_{B1})} \quad (4)$$

The correction factor $F_{\lambda corr}$ was determined as follows. A highly precise square glass cuvette with optical pathlength known to 0.1% as measured mechanically was used. A solution of dye B copper chloride with absorbance peak at 730 nm was introduced into the square cuvette and into a standard round vial. The absorbances were measured for the square cuvette and round vial at 730 nm. Then, the experiment was repeated with dye A Ponceau S at 520 nm. It was assumed that since the square cuvette has plane sides perpendicular to a well collimated light beam, there is no reason for a difference in pathlength between 730 nm and 520 nm in the square cuvette. The desired correction factor is thus given by $$F_{\lambda corr} = \frac{l_{520}}{l_{730}} = \frac{A \text{ round } (520)}{A \text{ square } (520)} - \frac{A \text{ square } (730)}{A \text{ round } (730)} \quad (5)$$

where A round (520), A square (520), A square (730) and A round (730) represent absorbance measurements of square cuvette and round vial at the indicated wavelengths. The results from a total of five such measurements are $F_{80\,corr}=1.0082\pm0.0002$. Care was taken to avoid moving the square cuvette or the round vial during the experiments since it would significantly reduce the accuracy of the results. All solutions were pipetted in and out, with the vial and cuvette remaining stationary in the photometer. The contents of the reference reagent cuvette 78 are mixed prior to measurement of absorbance in step 108, thereby stirring up any particles which may be present so that they are included in the zero measurement at 520 nanometers. Although the bottling procedure takes great care to avoid particulates in the vials, some particles are inevitably present. It is important that the zero measurement be taken under exactly the same conditions as the subsequent measurements. The results of the absorbance measurement is $A(0)$ and is expressed relative to the CAL A reading which was taken earlier in the day when the instrument was turned on. The value is not zero for three reasons:

a) The CAL A vial and the vial used for absorbance measurements during a volume calibration contain irregularities in the glass walls. The zero readings for two different vials or even the same vial after rotation can differ by 0.01. The difference is called $A_0$.

b) The zero on the photometer may have drifted over the intervening period of time since the CAL A vial was read. The instrument drift is included in $A_0$.

c) The reference solution of copper chloride has a small absorbance at 520 nm given by $\epsilon_{B1}C_B$ relative to the absorbance of the distilled water in the CAL A vial. Thus, $A_0$ is given by $$A_0 = A(o) - \epsilon_{B1} c_B l \quad (6)$$

After the vial pathlength has been determined as described above, measurements of pipette volume are taken. Referring again to FIG. 6, a pipette being calibrated having a volume $P_1$ is used to pipette an aliquot of sample solution containing dye A Ponceau S with concentration $C_A$ and absorptivity $\epsilon_{A1}$ at 520 nm to the reference reagent cuvette 78 in the photometer in step 114. The sample solution and the reference solution in the vial are mixed by the photometer in step 116 to form a mixture. The orientation of the vial in the photometer is not changed during this process so there is no reason for $A_0$ to change. The vial initially contained a volume $V_B$ of reference solution having dye B copper chloride at concentration $C_B$ and absorptivity $\epsilon_{B1}$ at 520 nm. The absorbance $A(1)$ of the vial containing the mixture at 520 nm is given by $$A(1) = A_0 + \frac{P_1 C_A \epsilon_{A1} l}{P_1 + V_B} + \frac{V_B C_B \epsilon_{B1} l}{P_1 + V_B} \quad (7)$$

The absorbance $A(1)$ is measured by the photometer in step 118 and all other corrections (i.e., temperature, etc.) are performed and the pipette volume is calculated in step 122. The pipette volume $P_1$ is the volume to be-determined in Equation (7). Solving Equations (6) and (7) for $P_1$ gives $$P_1 = V_B \frac{A(1) - A(0)}{(C_A \epsilon_{A1} l - C_B \epsilon_{B1} l) - (A(1) - A(0))} \quad (8)$$

All quantities on the right side of Equation (8) are known or have been measured, thereby permitting pipette volume $P_1$ to be calculated.

After the pipette volume $P_1$ has been calculated, the volume measurement process is repeated a predetermined number of times. This is done to verify the repeatability of the pipette operation and also to provide a more accurate determination of pipette volume. Typically, ten volume measurements are taken. After the first volume calculation is completed in step 122, the number of sample readings is checked in step 124. When less than ten sample readings have been completed, the pipette being calibrated is used to transfer a second aliquot $P_2$ of sample solution to the reference reagent cuvette 78 in the photometer. Importantly, the reference reagent cuvette 78 is not emptied or moved from the photometer between volume measurements, thereby insuring that the optical pathlength does not change due to rotation or other movement of the cuvette. The cuvette now contains a volume $P_1+P_2$ of sample solution. The volume $P_2$ of the second sample solution is calculated in accordance with $$P_2 = V_B \frac{A(2) - A(0)}{(C_A \epsilon_{A1} l - C_B \epsilon_{B1} l) - (A(2) - A(0))} - P_1 \quad (9)$$

where $A(2)$ is the measured absorbance of the vial after the volume $P_1+P_2$ of sample solution is added. Since $P_1$ is already known, $P_2$ can be calculated. The process is repeated until the desired number of pipette volumes have been measured. The limit as to how many pipette volumes can be added to the reference solution is either a) the absorbance of the cuvette contents should not exceed A=1.40 or there will be excessive non-linearity, or b) the contents of the cuvette should not exceed 9.75 milliliters or the mixing action will not be sufficient to insure homogeneity.

After all volume measurements have been taken, statistics are calculated in step 126. The statistics can include average, standard deviation and coefficient of variation. Then the results, including pipette serial number, nominal volume, individual volume readings and statistics, are printed in step 128. The user then removes the cuvette from the photometer, thereby making the photometer ready to begin another volume calibration sequence.

The dyes A and B used in the pipette calibration system have a dependence of absorbance on temperature. Temperature dependence was measured for both dyes using a Varian Cary Model 219 Spectrophotometer equipped with a temperature controlled cuvette holder. The absorbance of both dyes was measured in the range of 15° C. to 30° C. The temperature dependence of the absorptivity was found to be linear and of the form $$\epsilon(T) = \epsilon_{15}(1 + K(T - 15)) \quad (10)$$

where $\epsilon(T)$ represents the value of the absorptivity at temperature T, $\epsilon_{15}$ represents the value of the absorptivity at 15° C. and K is a constant. The values determined for K were $K_A = -0.05\%/°C$ and $K_B = 0.164\%/°C$. The temperature of the dyes as they are used during a pipette calibration is established by requiring that they be stored at the same ambient temperature as the photometer. The photometer accurately measures ambient room temperature at the beginning of a volume calibration in step 104 and thus also measures the temperature of the dyes.

All raw absorbance data as measured at ambient temperature T is corrected to 25° C. using the relationship $$A_{corrected} = A_{measured} \left( \frac{1 + K(25 - 15)}{1 + K(T - 15)} \right) \quad (11)$$

The concentrations of the dyes are adjusted so that correct pipette calibration results (without temperature correction factors being applied) are obtained at an ambient temperature of 25° C. The vials are filled with 4.8563±0.0025 grams of dye B solution, which occupies a volume of 4750 microliters at 25° C.

The volume of dye B at volume calibration time is dependent on its temperature according to $$V_B(T)=V_B(25°)(1+K_V(T-25)) \tag{12}$$

where $V_B(25°)=4750$ microliters and $K_V=2.32\times10^{-4}$ per °C. Thus, $V_B(T)$ can be calculated and used in the calculation of pipette volume. The value of $K_V$ is taken to be equal to the volume expansion coefficient for water as obtained from the *Handbook of Physics and Chemistry*.

In order to correct the volume calibration system for temperature effects, two corrections must thus be made: a) both dyes must be corrected for the dependence of their absorptivities on temperature, and b) the volume of dye B must be corrected for its dependence on temperature. Using these factors, the volume calibration system has been found experimentally to be corrected within 0.5% overall accuracy for the temperature range of 18° C. to 28° C.

Figure 7:
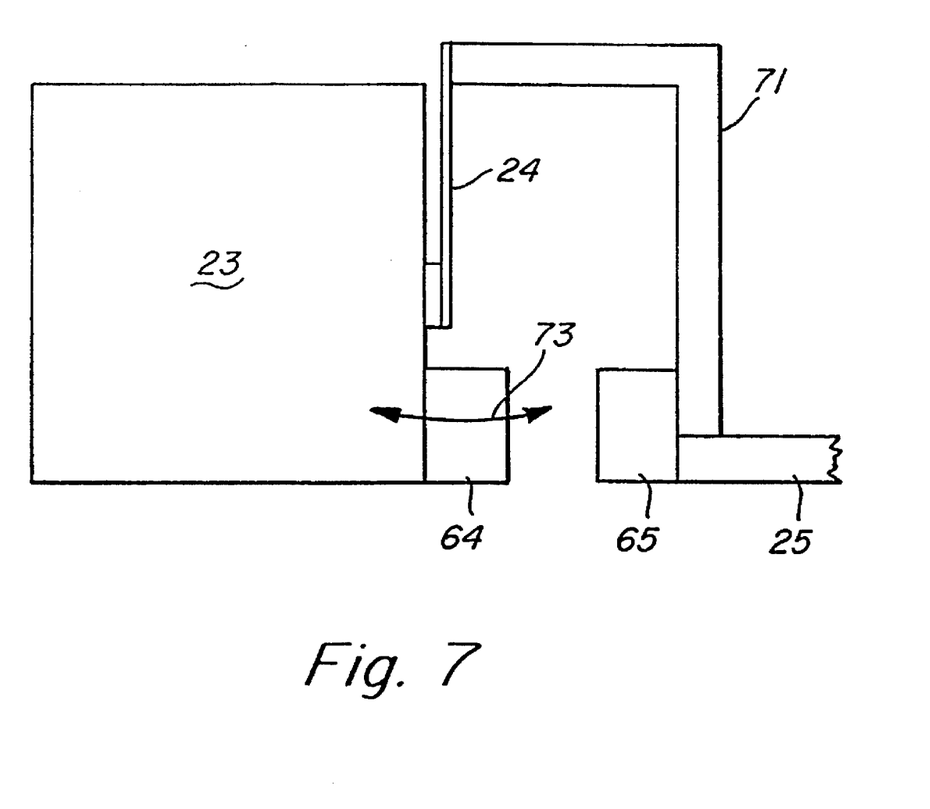
FIG. 7 is a block diagram of a resonant frequency mixing apparatus in the photometer as used in this invention.

FIG. 7 is a block diagram showing a preferred resonant frequency mixing apparatus, such as that described in the aforementioned U.S. Pat. No. 5,092,677, which is incorporated herein by reference.

In order to provide for resonant frequency mixing of the contents of the cuvette 27 while disposed in the photometer, the entire optical assembly 23 (shown in FIG. 3) is mounted on a leaf spring 24 and is fitted with a permanent magnet 64 which reacts to an energized electromagnet 65 mounted via support arm 71 on the instrument baseplate 25. Electromagnetic coupling between the electromagnet and the permanent magnet causes an oscillatory motion of the optical assembly in the direction of arrow 73. The electromagnet is activated to drive the optical assembly 23 at its resonant frequency for optimum mixing of the contents of the cuvette.

As described above, dye B comprises copper chloride having an absorbance peak at 730 nm and dye A comprises Ponceau S having an absorbance peak at 520 nm. It will be understood that other dye combinations can be utilized within the scope of the present invention. In general, the requirements on the selection of dye A and dye B include safety for the user, environmental safety, stability, lack of reaction between dye A and dye B, peak absorbances in the visible wavelength range and relatively small overlap of the absorbance spectra. Thus, dyes A and B can comprise any of a wide variety of organic and inorganic dyes or absorbance media, provided that they have absorbance spectra with little mutual overlap as shown in FIG. 5. The measurement wavelengths are typically selected to correspond with the absorbance peaks of dye A and dye B. Furthermore, the photometer shown in FIGS. 1, 3 and 4 and described above is not necessarily utilized. Any instrument capable of accurate absorbance measurements can be utilized within the scope of the invention. The microprocessor used for calculating optical pathlengths and volume can be separate from the photometer if desired.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A reagent system for determining the volume of a vessel which comprises:

a) a reference solution having a known volume comprising a first pH buffer, a first preservative solution, an anti-agglomeration agent, and a known concentration of an absorbing species having a first maximum absorbance peak; and b) a sample solution which comprises a second pH buffer, a second preservative solution, and a known concentration of an organic dye, the organic dye having a second maximum absorbance peak substantially different from the first maximum absorbance peak.

2. The system of claim 1, in which the dye is Ponceau S.

3. The system of claim 1, in which the first preservative agent comprises a mixture of methylparaben, phenoxytol, and EDTA,TSS.

4. The system of claim 1, in which the second preservative agent comprises a mixture of methylparaben, phenoxytol, and EDTA,TSS.

5. The system of claim 1 in which the anti-agglomeration agent is selected from among the group consisting of ethylene glycols, diethylene glycols, triethylene glycols, polyethylene oxides, polyethylene glycols, pyridines, and propylene glycols.

6. The system of claim 5 in which the anti-agglomeration agent comprises a polyethylene glycol having a molecular weight between about 200 and 10,000.

7. The system of claim 1, in which the first buffer is a phthalate buffer.

8. The system of claim 7 in which the phthalate buffer has a concentration in the range of approximately 0.01M to 0.1M, and a pH in the range of approximately 4 to 6.2.

9. The system of claim 1, in which the second buffer is a phthalate buffer.

10. The system of claim 9 in which the phthalate buffer has a concentration in the range of approximately 0.01M to 0.1M, and a pH in the range of approximately 4 to 6.2.

11. The system of claim 1, in which the absorbing species comprises a copper salt.

12. The system of claim 11, in which the copper salt comprises copper chloride.

13. The system of claim 11 in which the reference solution further includes a chelating agent for copper ions.

14. The system of claim 13 in which the chelating agent for copper ions comprises EDTA,TSS.

* * * * *

UNITED STATES PATENT AND TRADEMARK OFFICE
CERTIFICATE OF CORRECTION

PATENT NO. : 5,492,673
DATED : February 20, 1996
INVENTOR(S) : Curtis et al.

It is certified that error appears in the above-indentified patent and that said Letters Patent is hereby corrected as shown below:

Col. 6, line 53. - Should be designated (1) instead of (2)

Col. 11, line 7 - delete "$F_{80}$" and substitute -- $F_\lambda$ --.

Col. 11, line 55 - delete Equation (7) and substitute therefore $$A(1) = A_0 + \frac{P_1 C_A \epsilon_{A1}^0}{P_1 + V_B} + \frac{V_B C_B \epsilon_{B1}^0}{P_1 + V_B} \qquad (7)$$

Signed and Sealed this

Twenty-ninth Day of April, 1997

Attest:

BRUCE LEHMAN

Attesting Officer

Commissioner of Patents and Trademarks